United States Patent
Erbe et al.

(10) Patent No.: US 10,485,897 B2
(45) Date of Patent: Nov. 26, 2019

(54) OSTEOGENIC AND ANGIOGENIC IMPLANT MATERIAL

(71) Applicants: Erik Erbe, Chesterfield, MO (US); Anthony Ruggiero, San Juan Capistrano, CA (US)

(72) Inventors: Erik Erbe, Chesterfield, MO (US); Anthony Ruggiero, San Juan Capistrano, CA (US)

(*) Notice: Subject to any disclaimer, the term of this patent is extended or adjusted under 35 U.S.C. 154(b) by 330 days.

(21) Appl. No.: 15/290,586

(22) Filed: Oct. 11, 2016

(65) Prior Publication Data

US 2017/0112959 A1 Apr. 27, 2017

Related U.S. Application Data

(60) Provisional application No. 62/240,259, filed on Oct. 12, 2015.

(51) Int. Cl.

| *A61F 2/44* | (2006.01) |
| *A61L 27/56* | (2006.01) |
| *A61L 27/46* | (2006.01) |
| *A61F 2/30* | (2006.01) |

(52) U.S. Cl.
CPC ............ *A61L 27/56* (2013.01); *A61F 2/44* (2013.01); *A61F 2/4455* (2013.01); *A61L 27/46* (2013.01); *A61F 2002/30013* (2013.01); *A61F 2002/30064* (2013.01); *A61F 2002/3092* (2013.01); *A61F 2002/3093* (2013.01); *A61F 2002/30971* (2013.01); *A61F 2310/00179* (2013.01); *A61F 2310/00329* (2013.01); *A61L 2400/12* (2013.01); *A61L 2430/38* (2013.01)

(58) Field of Classification Search
CPC .......... A61F 2/4455; A61F 2002/30013; A61F 2002/30064; A61F 2002/3092; A61F 2002/3093; A61F 2310/00179; A61F 2310/00329; A61L 2400/12; A61L 2430/38; A61L 27/56; A61L 27/46
USPC ............................................ 623/17.11–17.16
See application file for complete search history.

(56) References Cited

U.S. PATENT DOCUMENTS

| 7,972,434 B2* | 7/2011 | Engqvist ................. A61L 27/12 106/711 |
| 8,647,614 B2* | 2/2014 | Clineff et al. .......... A61L 27/44 424/78.08 |
| 2003/0125739 A1* | 7/2003 | Bagga ................... A61F 2/4455 606/247 |

(Continued)

*Primary Examiner* — Kevin T Truong
*Assistant Examiner* — Jessica Weiss
(74) *Attorney, Agent, or Firm* — C. John Brannon; Brannon Sowers & Cracraft PC (57) ABSTRACT

A spinal implant body 100, including a body volume 101 having an inferior portion 102A, a superior portion 102B, and a central portion 102C disposed between the inferior and superior portions 102A, 102B. The body 100 further includes a first bioactive polymer portion 117A distributed throughout body volume 101, a second bioactive ceramic portion 120A distributed throughout the body volume 101, and a third interconnected pore network portion 105A (which may be filled with a fourth fugitive portion 140A) distributed throughout the body volume 101. The central portion 102C is less porous than the inferior and superior portions 102A, 102B and the pores in the inferior portion 102A are on average larger than the pores in the central portion 102C.

2 Claims, 6 Drawing Sheets

(56) References Cited

U.S. PATENT DOCUMENTS

| | | | |
|---|---|---|---|
| 2003/0138473 A1* | 7/2003 | Koblish | A61B 17/866 424/423 |
| 2004/0193270 A1* | 9/2004 | DiMauro | A61F 2/447 623/17.11 |
| 2004/0230309 A1* | 11/2004 | DiMauro | A61F 2/28 623/17.12 |
| 2005/0049706 A1* | 3/2005 | Brodke | A61F 2/30767 623/17.11 |
| 2005/0177238 A1* | 8/2005 | Khandkar | A61F 2/30767 623/17.11 |
| 2005/0209603 A1* | 9/2005 | Zucherman | A61B 17/7053 606/90 |
| 2005/0209696 A1* | 9/2005 | Lin | A61F 2/441 623/17.12 |
| 2006/0015184 A1* | 1/2006 | Winterbottom | A61F 2/44 623/18.11 |
| 2006/0036316 A1* | 2/2006 | Zeltinger | A61L 31/18 623/1.49 |
| 2007/0191963 A1* | 8/2007 | Winterbottom | A61F 2/28 623/23.5 |
| 2007/0213827 A1* | 9/2007 | Arramon | A61F 2/4455 623/17.11 |
| 2009/0098183 A1* | 4/2009 | Detamore | C12N 5/0075 424/423 |
| 2009/0148348 A1* | 6/2009 | Pettigrew | C08J 7/12 422/400 |
| 2010/0004745 A1* | 1/2010 | Deslauriers | A61F 2/447 623/17.12 |
| 2010/0137990 A1* | 6/2010 | Apatsidis | A61B 17/866 623/17.16 |
| 2011/0015743 A1* | 1/2011 | Deslauriers | A61F 2/4455 623/17.16 |
| 2011/0046732 A1* | 2/2011 | Dyke | A61K 35/22 623/13.11 |
| 2011/0106272 A1* | 5/2011 | Liu | A61F 2/28 623/23.61 |
| 2012/0040015 A1* | 2/2012 | Lehtonen | A61L 27/446 424/602 |
| 2012/0097194 A1* | 4/2012 | McDaniel | A01N 63/02 134/26 |
| 2012/0150299 A1* | 6/2012 | Ergun et al. | A61F 2/442 623/17.11 |
| 2012/0237568 A1* | 9/2012 | Murphy | A61L 27/446 424/400 |
| 2013/0138221 A1* | 5/2013 | Junker | A61K 31/675 623/23.57 |
| 2013/0178947 A1* | 7/2013 | Monaghan et al. | A61L 27/56 623/23.55 |
| 2013/0274886 A1* | 10/2013 | Matsumoto | A61F 2/442 623/17.16 |
| 2014/0236299 A1* | 8/2014 | Roeder | A61F 2/28 623/17.16 |
| 2015/0238325 A1* | 8/2015 | Liu | A61F 2/28 623/17.16 |

* cited by examiner

OSTEOGENIC AND ANGIOGENIC IMPLANT MATERIAL

CROSS-REFERENCE TO RELATED APPLICATIONS

This patent application claims priority to U.S. Provisional Patent Application Ser. No. 62/240,259, filed on Oct. 12, 2015.

TECHNICAL FIELD

The novel technology relates generally to materials science, and, more particularly, to a high surface area graphene composite material.

BACKGROUND

Novel composite materials have been developed that represent a significant evolution over existing implant materials, such as polyetheretherketone (PEEK), which can impart strength to physiologic environments requiring load bearing support, such as, for example, interbody spine implants. One advantage of PEEK and like materials is that they provide good osteogenic and angiogenic properties which reduce fibrous tissue encapsulation and render radiopacity more appropriate for determination of the orientation of the implant.

Incorporation of bioactive ceramic fillers and/or minerals into the base polymer structure is a method that yields consistent mechanical property retention, while simultaneously increasing the ability of the material to bond to bone after implantation. This bonding to bone at key interfaces leads to improved fusion stability, pain relief and accelerated healing. The addition of specific bioceramic materials, such as borate glass, ceramics and glass-ceramics, having a variety of compositional flexibilities, but essentially consisting of any bioactive class of ceramics.

Use of precise placement of these bioactive components into the superior and inferior (opposing) surfaces of an implant, as well as the interior column, would allow for accelerated load transduction, clear orientation of the implant radiographically. The time related healing and bonding of bone tissue to these implants will lend itself to sustained microenvironment conducive to bone apposition and supportive angiogenesis, where vasculature is challenged, but required for consistent bone formation.

Previous attempts to augment or create a bonding interface have included addition of titanium metal, porous interfaces and HA (hydroxyapatite ceramics). While useful, these improvements have been limited. Further, tissue bonding and regrowth remains a slow and painful process. There remains a need for implant materials that give rise to improved bonding speed and strength as well as improved and more complete osteogenesis/angiogenesis. The present novel technology addresses this need.

DESCRIPTION OF PREFERRED EMBODIMENTS

For the purposes of promoting an understanding of the principles of the novel technology, reference will now be made to the embodiments illustrated in the drawings and specific language will be used to describe the same. It will nevertheless be understood that no limitation of the scope of the novel technology is thereby intended, such alterations and further modifications in the illustrated device, and such further applications of the principles of the novel technology as illustrated therein being contemplated as would normally occur to one skilled in the art to which the novel technology relates.

Overview

The present novel technology relates to multicomponent bioactive ceramic (bioglass)-polymer matrix composites with sufficient strength to bear load in the human skeleton, especially the spine, allowing for bone apposition, integration and incorporation. This approach is tailorable to increase porosity (and, accordingly, surface area) up to 80% or even 90% or more, while maintaining sufficient strength to support and bear load, thus allowing for physiologic integration. This integration can be with hard or soft tissue, typically bone formation for hard tissue and muscle and/or collagen formation and growth with soft tissue integration. Some illustrations of hard tissue integration applications of the present novel technology are spine implants, long bone anchors, implants, interference screws (both in hard and soft tissue), tendon augmentation, bone-tendon interface augmentation or coupling, replacement of soft tissue defects requiring muscle attachment (such as with eye balls), and the like.

The instant novel composites may be formed and tailored to have uniform, predetermined, or random gradient orientations of bioactive fillers, particle size distributions, particle shapes, particle shape distributions, porosity, porosity distributions, and neat regions of pure polymer-matrix, depending on a desired target configuration. Bioactive particles with higher surface area and/or more edges dissolve faster and thus promote faster healing and regrowth while yielding the formation of porosity at a faster pace, which also tends to lower strength. Thus, the selection of the distribution of particle size, shape and surface area allows for the selection of desired and predetermined growth and strength curves for the implant 100.

Layered and/or gradient composites 150 may be formed that would range from highly porous, highly bioactive at the outer surfaces to less porous, less bioactive in the core of the material. This flexibility is achieved via adjustment of the particle size, particle size distribution and shape of the bioactive particle additives 120, of fugitive (typically salt) additives 140 and the parent polymer-matrix (PEEK) particles 117. In addition to PEEK, other biocompatible, load bearing polymer matrices (for example, PEEKEK and PLLA) are useful.

Figure 4A:
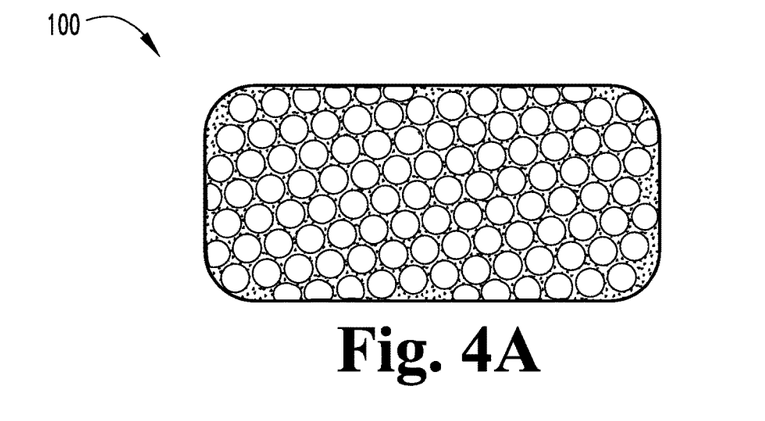
FIGS. 4A-4C are side elevation sectional views of uni-modal, bi-modal and tri-modal particle size distributions as they pertain to the present novel technology.
Figure 4B:
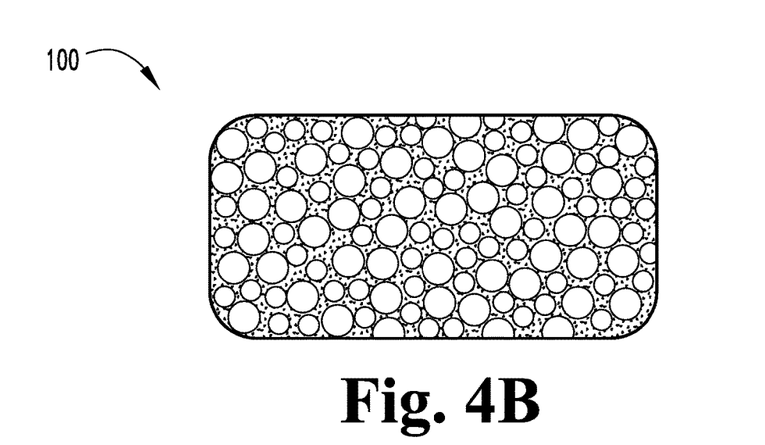
Figure 4C:
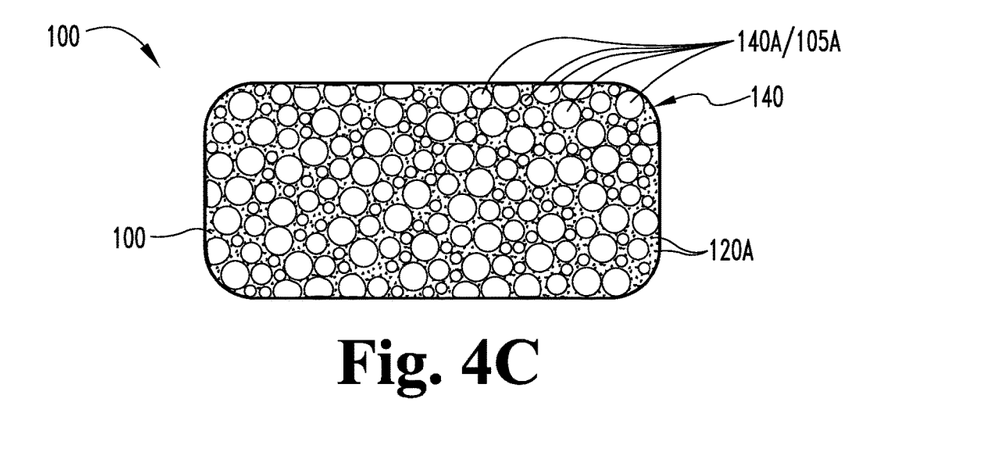
Figure 5A:
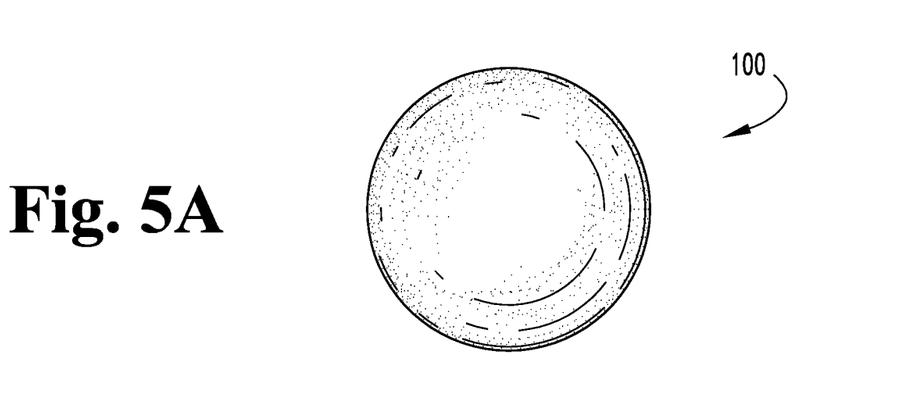
FIGS. 5A-5C are perspective views of various soft-tissue implants according to the present novel technology.
Figure 5B:
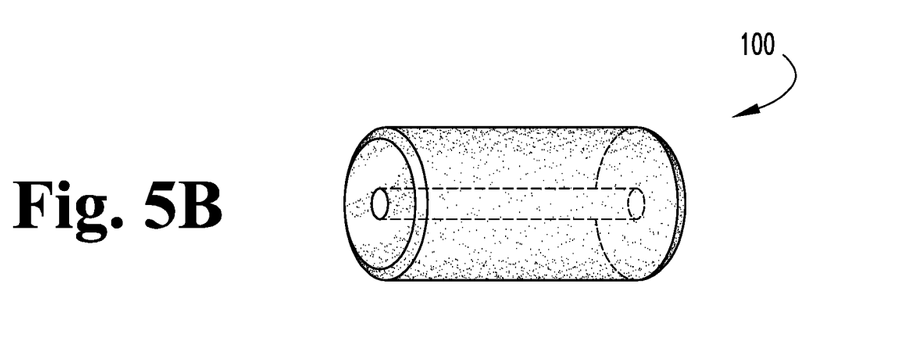
Figure 5C:
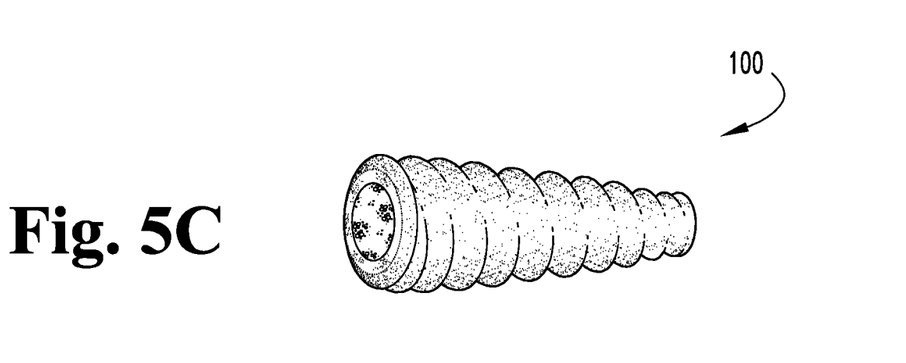

In one particular example composition, the PSD of the fugitive particles 140 is typically trimodal (blending of three distinct and narrow PSDs), the largest being about 600 microns, the middle being 200-400 microns, the smallest being 20-200 microns, such that smaller particles fill the interstices between larger particles. Bimodal and unimodal PSDs are also acceptable as would be greater multimode distributions, depending on the desired porosity, size and distribution of interconnected resulting void space (porosity) when the fugitive particles are removed. This flexibility allows for the increase/decrease of surface area, porosity and interconnectivity of the voids that are produced when the fugitive phase is dissolved away or leached out. The shape of these voids is as controlled by the choice of fugitive phase particle size and shape distributions, as is the interconnectedness of the resulting pore network. Rounded, spherical fugitive particles are typical, but oval, elliptical, cylindrical (rounded geometry) particle shapes may also be beneficial, especially compared to square or sharp edged configurations that are typically less desirable for most cellular microenvironments, attachment, and physiologic fluid flow.

In addition to the imparting of surface bioactivity by the incorporation of bioactive ceramics 120 to the composition of the novel composite material 150, another benefit derived from the use of such materials is radiographic illumination of areas of the implant that have greater amounts of bioactive additive. Radiographic orientation of the implant is helpful for successful placement. PEEK, typically the parent matrix-polymer of the composite material is inherently radiolucent, meaning that it is nearly transparent to x-ray imaging making orientation determination post-surgery challenging. Addition of bioactive ceramics 120, in particular at the superior (upper) and inferior (lower) implant surfaces, allows for improved radiodensity allowing for imaging and visualization of the implant orientation in the human body at the implant site.

The radiopacity can be tailored from near radiolucent (nearly invisible under x-ray imaging) up to the radiodensity of human cancellous bone. Greater radiopacity is typically not desired, as assessing the growth of new bone throughout the implant body becomes more difficult if the radiopacity of the implant 100 is too high (greater than the native cancelleous bone). More typically the upper, lower and interior surfaces of the implant 100 are more radiodense than the body of the implant 100, which allows for the location and orientation of the implant to be readily assessed radiographically.

Similarly, the mechanical properties are tailorable, relative to native cancellous and cortical bone. While the traditional solid and nonporous PEEK implants are nearly matched to the strength, toughness and modulus of cortical, cancellous geometries found in the human body, the instant implant 100 incorporates bioactive glass fillers, porosity and ultimate physiologic integration to make the time-zero properties starting points while the overall properties are dynamic as the physiologic bone formation and integration adds mechanical benefit to the implanted construct. Modulus, strength and toughness are typically increased with the addition of bioactive fillers 120, which also typically increase with time post-implantation due to the incorporation of new bone tissue. Though porosity 105 can initially decrease the strength parameters, strength is still sufficiently high at time-zero to warrant augmenting human bone and will increase quickly and significantly as new bone apposition occurs quickly, allowing for stress sharing at the bone-implant interface.

Porosity within these implants 100 typically mimics human cancellous bone, in that the range of pores size is generally nanometer to millimeter, interconnected, rounded and all affording a greater surface area, per cross-sectional, axial area under load, that has exposed bioactive glass filler particles allowing for osteogenesis, angiogenesis and formation of nanocrystalline CaP bone precursors.

FIGS. 1A-6 illustrate a first embodiment of the present novel technology, implant devices 100 having radiopacity similar to that of bone or hard tissue and having variable and tailorable porosity 105 and bioactive compositional gradients 110 tailorable to a specific desired application and in vivo environment. The porosity 105 is typically open and interconnected, and more typically tailored to increase tissue (typically bone) bonding and tissue (typically bone) regrowth speed while reducing healing time and pain intensity and duration. The composite material 115 is typically PEEK or like polymer materials 117 blended with porous bioactive material 120, such as packed bioglass particles, flakes, and/or fibers, and the composition, particle size distribution (PSD), particle shape, particle aspect ratio, porosity, and/or density may be varied to optimize healing time and pain relief, as well as to foster complete bridging of regrown tissue/bone, provide sufficient load bearing compressive strength, maximize tissue bonding, connection time, and bond strength to hard and/or soft tissue, and to drive healing by promoting specific cell phenotypes.

Some differentiation features of the composite material 115 allow for accelerated healing, bone formation and apposition. This is typically achieved with accelerated reduction of micromotion, limited fibrous encapsulation of the implant 100, and preferred orientation evaluation due to the material 115 exhibiting sufficient radiopacity. The blending of bioactive fillers 120 at the interface surfaces 125 yields a gradient material no as the outermost surface will have more filler 120 than what is present in the middle of the material no. Improvement of the base PEEK implant material 117, though attempted in other formats (HA and Ti) have not achieve successful levels of ostoegenicity, angiogenesis and surface integration. The materials, compositions and ultimate composition of matter of the instant composites 115 provide a unique platform for improved implant healing, performance and integration physiologically.

The instant multicomponent composites 115 are useful for orthopedic, spinal and other general implant sites and benefit from more efficient, rapid and complete integration with, bonding to, and creation of bone apposition. The structure of the implant 100 is conducive to osteoconduction, typically having a porosity range between 100-500 microns. The creation of a bioactive interface 125 yielding an osteostimulatory and angiogenic microenvironment have been attained, at least in part, by the addition of bioactive ceramic, glass, glass-ceramic fillers, spheres, fibers, flakes and combinations thereof that yield mechanic strength, via composite principles, as well as modification of the implant surface 125 post implantation into the physiologic environment. The surface reaction is a departure from the native or neat surface reaction typical of PEEK materials, widely used in orthopedic, spine implants.

The surface modification of the implants 100 benefit from the tailored integration of bioactive fillers 125. Known bioactive ceramics, such as bioglasses, have utility in this composition 115. One typical bioglass composition of this invention is the borate bioglass analogue designated 13-93B3, which is in weight percent given by $$5.5Na_2O-11.1K_2O-4.6MgO-18.5CaO-3.7P_2O_5-56.6B_2O_3$$

which is known to be bioactive, osteostimulatory, and angiogenic. Another useful bioglass composition is, in weight percent, given by $24.5Na_2O$—$24.5CaO$—$6P_2O_5$—$45SiO_2$.

Other ceramics, HA, beta-TCPs, monetite, brushite precursor CaPs may also be selected as appropriate additives by those skilled in the art. The selection of the particular bioactive glass composition, accompanied with various elemental additives (such as Sr, Cu, Zn, Mg, and the like) can further facilitate a microenvironment more conducive to bone formation and apposition, as well as promote the development and growth of particular, predetermined cellular phenotypes. The bioglass materials may be provided as powder precursors, derived from sol-gels, or any like convenient precursor process.

This surface reaction occurring at the tissue/implant interface 125 (known as bioactivity or osteostimulation) illicits $Ca^{+2}$ and $PO_4^{-3}$ ion release into the microenvironment with the simultaneous change (to a negative) in surface charge. These surface reactions occur immediately upon implantation and may persist for weeks, or at least until the adjacent physiologic microenvironment interface has been converted to bone. The new bone-implant interface 125 will progress over time and transfer (transduce) mechanical loads through the interface 125, implant, and bone-implant system such as to avoid the formation of excessive fibrous tissue, encapsulation and resulting micromotion, implant loosening and possible failure. Additionally, the bioactive glass composition selected imparts angiogenesis or vessel formation, which also assists in the osteogenic process of bone formation, requiring blood, oxygen and cellular nutrients and protein precursors to infiltrate and support the surface reaction and microenvironment 130.

Also, the specific addition of bioactive glass particles adds radiopacity to specific, upper, lower, and interior surfaces. This allows for the imaging, position and orientation of the implant. This obviates the need for added Ta or Ti metal pins or markers needed in traditional PEEK implants.

The desired reaction rate can be achieved with many different bioactive particles compositionally and size-wise. Ideally the particle size is sufficiently small as to not degrade significantly the mechanical properties of the resulting implant. Bioactive particles less than 100 microns across are typical, more typically less than 45 microns, and still more typically less than 10 microns and down to nanometer size range. Combinations (typically bimodal or trimodal) of larger and smaller particles may yield tailored PSDs based on target levels of surface reactivity. Likewise, varied shapes of bioactive particle additives such as microspheres, irregularly shaped aggregates, fibers, rods, flakes, and combinations thereof all contribute to the efficacy of the implant 100 and may impart specific physical, chemical, biological and/or mechanical property benefits such as toughening, modulus adjustment and compressive strength. Coupling agents may or may not be used or required, but can be exploited to increase the particle polymer-matrix interface strength.

Control of the rate and extent of implant 100 bonding to surrounding tissue may be related to the exposure of the implant interface 125 and is derived from the creation of interconnected porosity 105 during manufacturing of the implant 100. The blending of a variety of component bioactive filler compositions, particle sizes, particle shapes, and/or PSDs yield various surface exposures of the incorporated bioactive glass as well as the generation of the interconnected porosity 105. One method used to generate controlled porosity 105 is achieved by the addition of fugitive materials 140, such as salts (typically NaCl) or other fugitive crystals, sugars, polysaccharides, combinations thereof, and the like, that can withstand the compression molding temperatures of the matrix polymer (PEEK) and subsequently be leached out of the implant 100 to yield voids and interconnected porosity 105 where desired in the final implant 100. The selection of the particle size, shape and distribution of the leachate fugitive component 140 is key to controlling the microstructure and nature of the interconnected porosity 105 and resulting microenvironment 130 for bone formation. Round, spherical fugitive salt particles are typically selected in the size range of 100-600 microns, in monodispersed, bi-modal and multimodal size distributions. The large fugitive particles yield larger cavities when dissolved away; the subsequent smaller fugitive particles that reside in between the large particles, when leached out, allow for interconnectedness of the voids and, thus, interconnected open porosity.

The weight percent of added bioactive particles is typically greater than 10%, more typically up to 20%, and still more typically between 20% and 60%, as increasing amounts of bioactive materials may lead to unacceptable decrease in strength, especially as the bioactive materials are dissolved. For applications requiring lower mechanical strength there is no practical limit, as long as at least 1-5% polymer-matrix persists for aggregate bonding.

Powder processing pre-molding impacts the distribution of the bioactive, polymer-matrix and fugitive phases 120, 140. The blend of multi-modally distributed particles will be compression molded at sufficient temperature, typically above 275 C, up to 350 C, to melt any polymer-matrix (PEEK) phase allowing for intimate incorporation and creation of the bulk composite 150. The bulk composite 150 can be formed and shaped by any convenient methodology, such as extrusion molded, near met-shape molded, cast or formed, machined or CNC formed into the near final implant shape. Any forming and/or machining is typically performed while the fugitive phase material is still in place (not yet leached out) as to prevent any machining, forming debris from becoming entrapped in the inner interstices of the implant 100. After machining and/or forming, the implant 100 is submerged into warm water, saline, or other appropriate solvent to remove the fugitive phase 140, leaving a typically interconnected network of porosity 105 in the composite 150 to yield a porous composition 115 typically comprised of PEEK polymer-matrix infiltrated with bioactive fillers 120 that now have a significant exposure on the newly created implant interface 125 and an interconnected porous microenvironment 130.

Powder blending relates to the addition of appropriate amounts of the respective filler particles, polymer powders, bioactive ceramic powders and fugitive salt powders. Typical blending and/or powder homogenization methods can be performed dry or with solvent assistance. When using solvents, residual solvents are typically removed prior to compression molding. Dispersion of the respective particles can be achieved using basic agitation, blending, shaker methods known well in powder processing.

In some embodiment, pre-conditioning or pre-reacting of the bioactive particles 120 is done to expose the surfaces of the implants 100 by soaking final implants 100 in PBS (Phosphate buffered Saline), SBF (simulated body fluids), or like solutions for appropriate periods of time to illicit the co-precipitation of nanocrystalline (CaP) HA precursors, CaPs on the surface of the composite prior to implantation. This can be done during manufacturing, after the salt leaching step, pre implantation and could accelerate protein, cell or drug attachment once implanted.

Figure 1A:
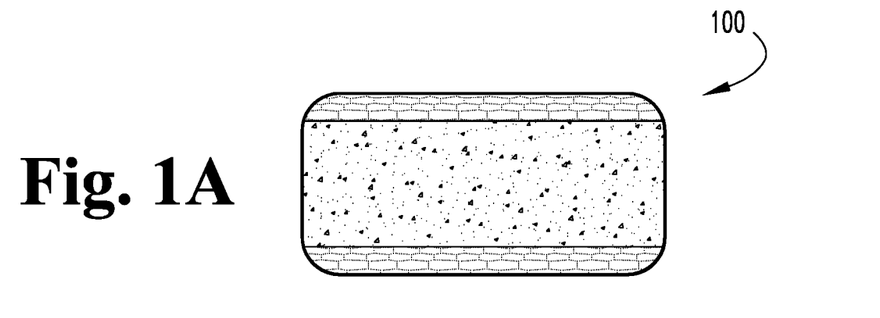
FIGS. 1A-1D are side elevation sectional views of various layered composite material configurations, including the porous and bioactive material configuration of a first embodiment of the present novel technology.
Figure 1B:
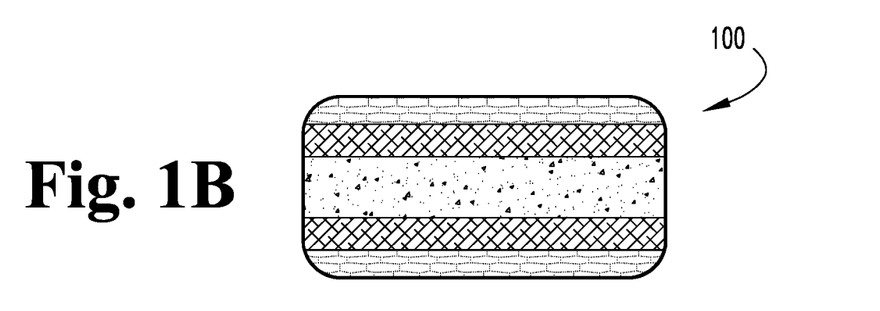
Figure 1C:
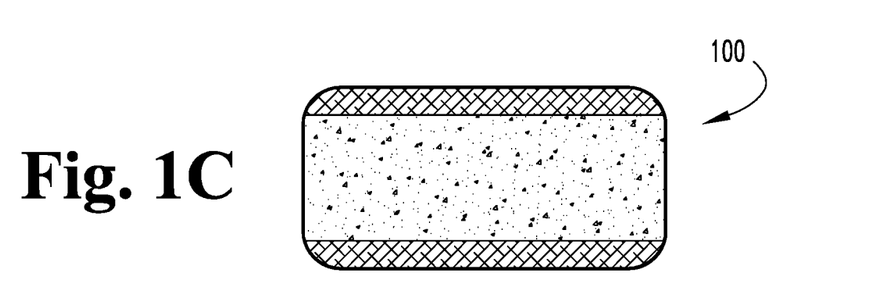
Figure 1D:
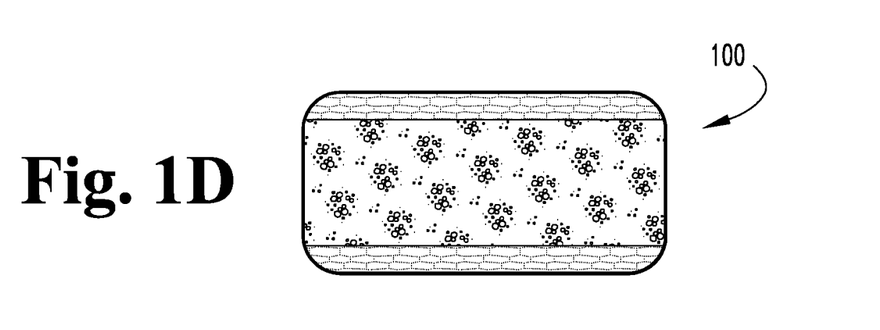
Figure 2A:
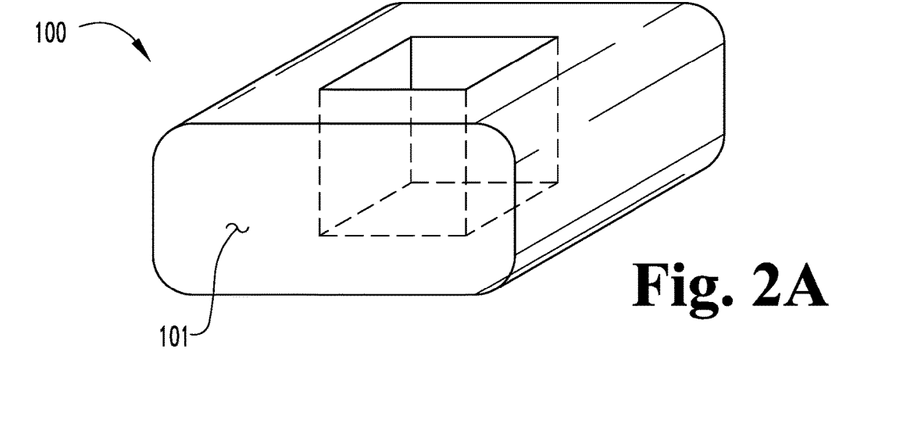
FIGS. 2A-2C are various perspective cutaway views of implants according to the present novel technology.
Figure 2B:
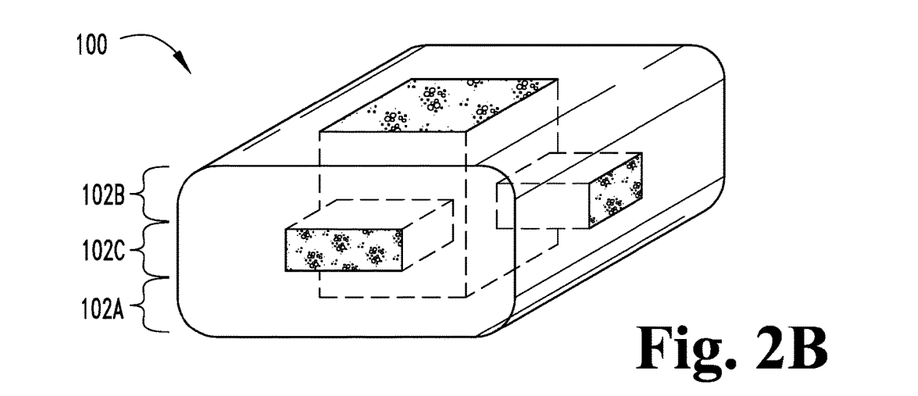
Figure 2C:
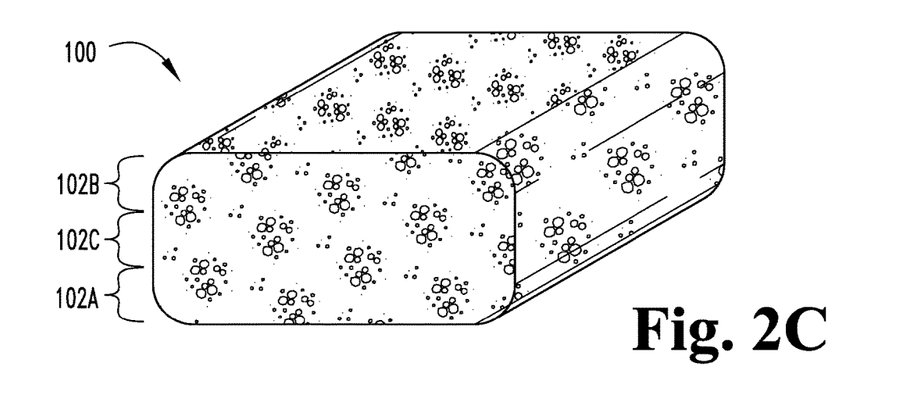
Figure 3A:
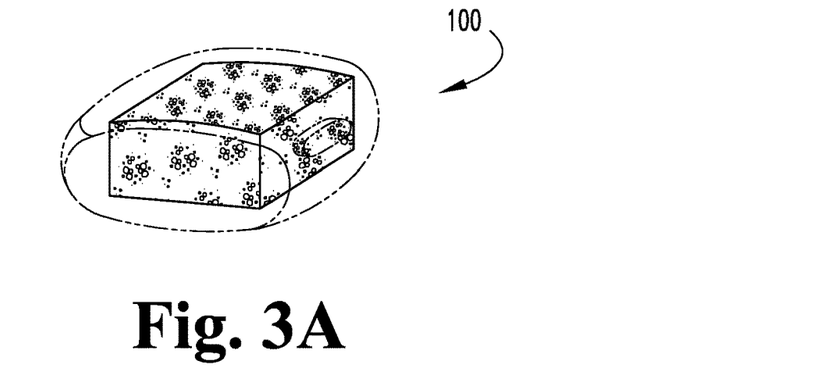
FIGS. 3A-3C are various perspective cutaway views of spinal implants according to the present novel technology.
Figure 3B:
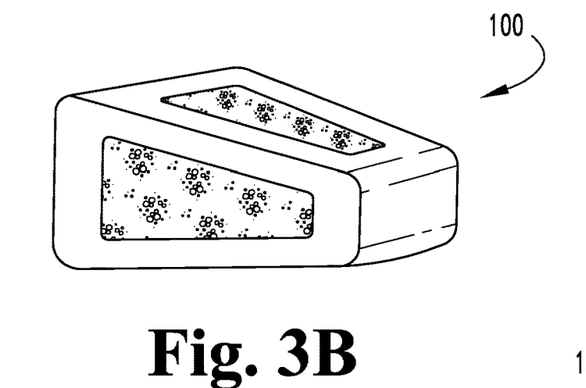
Figure 3C:
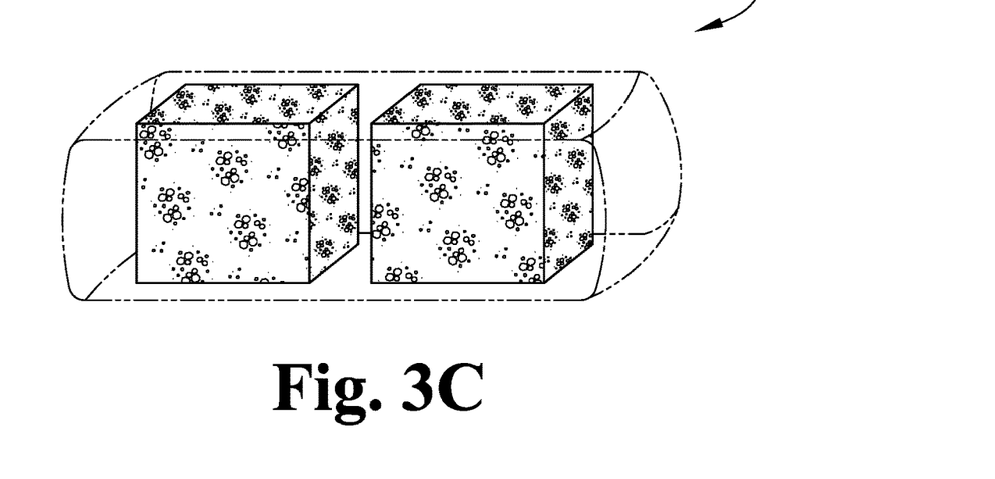

Adjustments to the orientation of the various particles combined in the pre-molding step can achieve gradient compositions that have inner cores of pure PEEK, interior surfaces of that inner core having higher percentages of the bioactive particles, thus allowing for multiple resulting surfaces having bioactivity while retaining the innate biomechanics of the polymer-matrix (typically PEEK). In particular, an interbody spine implant (IBFD) wo would be able to achieve bioactive interfaces in a composites superior, inferior and central-interior surfaces. The superior and inferior interfaces of the spine implant would be in direct contact with the bone of the adjacent vertebrae being "fused" and would exist in compression loading, which would facilitate the rapid formation of bone.

Additional methods of composite formation may be accomplished using the precursor powder blends described above, such as 3-D printing of layers using known methods. This would increase the 'tuneability' of the various layers, interfaces, surfaces and the achievement of precision, complex shapes and configurations.

Complex shapes, porosities and surface bioactivity may be achieved by using combinations of material, additives, fugitives, as well as shapes, sizes and PSDs of the particles, to yield implants 100 having superior surfaces and bulk characteristics for cell attachment, protein adsorption and drug or antibiotic incorporation at the time of implantation or during manufacture. Low-temperature post fugitive leachate and infusion allows for incorporation of temperature sensitive drugs, molecules or proteins.

Increased porosity can reduce the original strength expected from a neat implant (no pores), but even with significant porosity, such as up to 70% or even 80% or more, the implant body 100 can still retain sufficient strength, axial compression strength, shear strength, and elastic modulus acceptable for physiologic loading in the human skeleton, and, in particular, the spine. The incorporation of bioactive fillers 120 can increase the elastic modulus of the resultant body 100 and by promotion of bioactivity, bone apposition at the interface 125 can lead to an increase in the overall strength and load capacity of the implant-bone system. Thus, increased porosity 105 increases the surface area exposed to the physiologic microenvironment 130 that promote bone formation, apposition, angiogenesis and ultimately implant-bone stability. The instant implants 100 have increased surface area for bioactivity per axial area in between bone segments to be fused and loaded.

Figure 6:
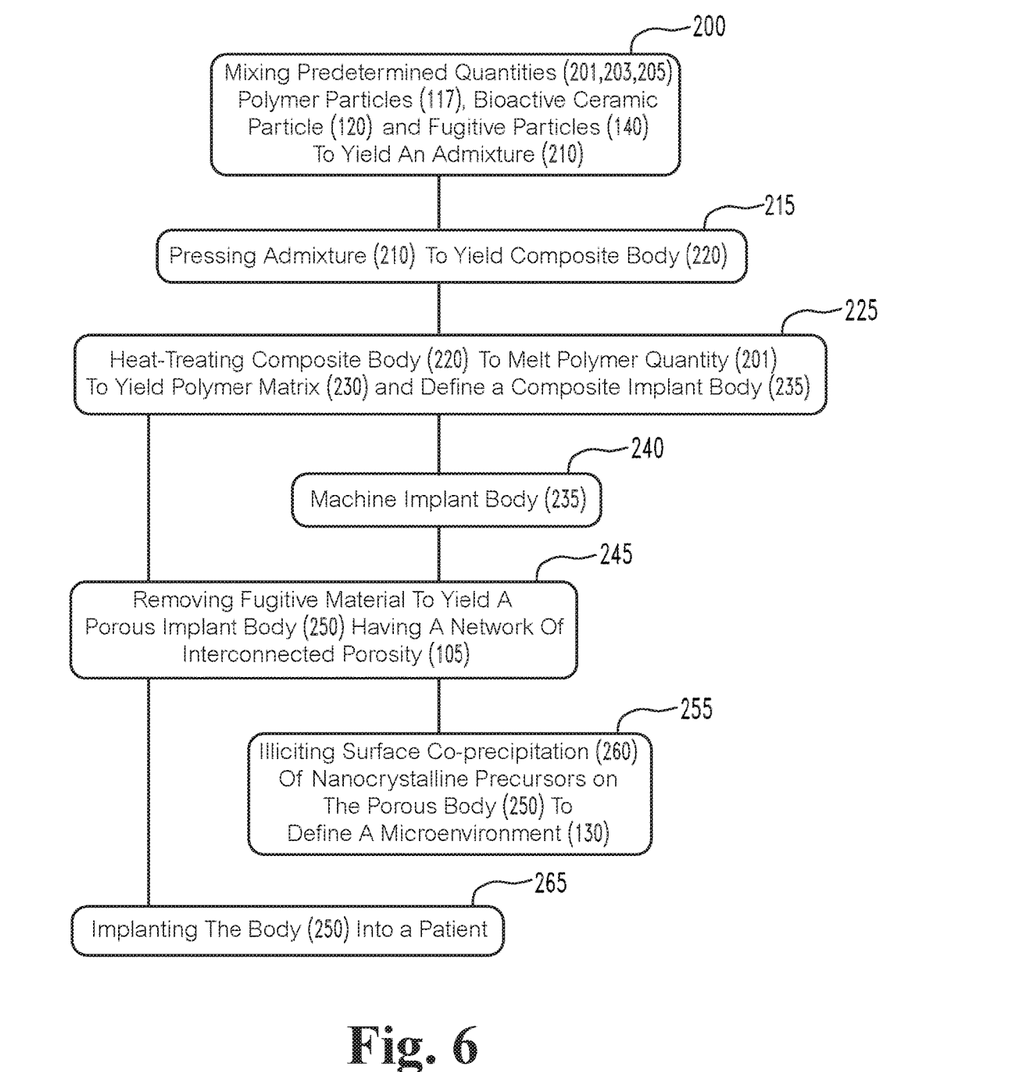
FIG. 6 is a flow chart representing a method for the preparation of the implant devices of the present novel technology.

In operation, the implant 100 is produced by first mixing 200 a first quantity 201 of bioactive polymer particles 117, a second quantity 203 of bioactive ceramic particles 120, and a third quantity 205 of fugitive material particles 140 to define an admixture 210. The relative amounts of each portion 201, 203, 205, as well as the sizes, PSDs, shapes, shape distributions, and compositions thereof, are selected to cooperate to yield a predetermined degree and distribution of porosity, a predetermined target dissolution rate of the bioactive portions, and a predetermined target strength of the implant 100. The admixture 210 is pressed or otherwise formed 215 to define a green or composite body 220, which is then heat-treated 225 or calcined to melt the first quantity 201 of bioactive polymer particles 117, defining a calcined composite implant body 235 having bioactive ceramic particles 120 and fugitive material particles 140 bound in a bioactive polymer matrix 230. The calcined body 235 may then be machined or otherwise formed 240 to a desired shape, if necessary. The calcined body 235 is then infiltrated with a solvent to remove 245 the fugitive material particles 140 to yield a network of interconnected pores 105 and to define a porous calcined body 250 ready for implanting 265 into a patient. The network of interconnected pores 105 may be thought of as being preexisting and filled with the fugitive material particles and/or the bioactive particles. Optionally, prior to implantation 265, the surface co-precipitation 260 of nanocrystalline (CaP) HA precursors on the porous calcined body 250 may be illicited.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

We claim:

1. A spinal implant body of comprising:
   a body having a body volume, an inferior portion, a superior portion, and a central portion disposed between the inferior and superior portions;
   a first biocompatible polymer portion distributed throughout the body;
   a second bioactive ceramic portion distributed throughout the body;
   a third interconnected pore network portion distributed throughout the body; and
   a fourth fugitive portion filling the third interconnected pore network;
   wherein the central portion is less porous than the inferior and superior portions;
   wherein a mean pore size of-pores in the inferior portion is greater than a mean pore size of-pores in the central portion; and
   wherein the fourth fugitive portion has a bimodal size distribution.

2. A spinal implant body comprising:
   a body having a body volume, an inferior portion, a superior portion, and a central portion disposed between the inferior and superior portions;
   a first biocompatible polymer portion distributed throughout the body;
   a second bioactive ceramic portion distributed throughout the body;
   a third interconnected pore network portion distributed throughout the body; and
   a fourth fugitive portion filling the third interconnected pore network;
   wherein the central portion is less porous than the inferior and superior portions;
   wherein a mean pore size of-pores in the inferior portion is greater than a mean pore size of-pores in the central portion; and
   wherein the fourth fugitive portion has a trimodal size distribution.

* * * * *

UNITED STATES PATENT AND TRADEMARK OFFICE
CERTIFICATE OF CORRECTION

PATENT NO. : 10,485,897 B2
APPLICATION NO. : 15/290586
DATED : November 26, 2019
INVENTOR(S) : Erik Erbe et al.

Page 1 of 1

It is certified that error appears in the above-identified patent and that said Letters Patent is hereby corrected as shown below:

In the Claims

Column 8, Line 27 please delete "of" after "body".

Signed and Sealed this
Seventh Day of January, 2020

Andrei Iancu
*Director of the United States Patent and Trademark Office*